United States Patent
Naidu et al.

(10) Patent No.: US 7,197,172 B1
(45) Date of Patent: Mar. 27, 2007

(54) DECOMPOSITION OF MULTI-ENERGY SCAN PROJECTIONS USING MULTI-STEP FITTING

(75) Inventors: Ram Naidu, Waban, MA (US); Ibrahim Bechwati, Waltham, MA (US); Carl R. Crawford, Brookline, MA (US)

(73) Assignee: Analogic Corporation, Peabody, MA (US)

( * ) Notice: Subject to any disclaimer, the term of this patent is extended or adjusted under 35 U.S.C. 154(b) by 805 days.

(21) Appl. No.: 10/611,572

(22) Filed: Jul. 1, 2003

(51) Int. Cl.
*G06K 9/00* (2006.01)
*G01N 23/04* (2006.01)

(52) U.S. Cl. ........................................ 382/131; 378/62

(58) Field of Classification Search ................ 382/131, 382/132; 250/252.1, 339; 378/4, 7, 53, 378/54, 62, 68, 86–88
See application file for complete search history.

(56) References Cited

U.S. PATENT DOCUMENTS

| | | | |
|---|---|---|---|
| 4,029,963 A | 6/1977 | Alvarez et al. | |
| 4,759,047 A | 7/1988 | Donges et al. | |
| 4,884,289 A | 11/1989 | Glockmann et al. | |
| 5,132,998 A | 7/1992 | Tsutsui et al. | |
| 5,182,764 A | 1/1993 | Peschmann et al. | |
| 5,247,561 A | 9/1993 | Kotowski | |
| 5,293,195 A * | 3/1994 | Berlad et al. ................. 378/87 |
| 5,319,547 A | 6/1994 | Krug et al. | |
| 5,367,552 A | 11/1994 | Peschmann | |
| 5,473,657 A | 12/1995 | McKenna | |
| 5,490,218 A | 2/1996 | Krug et al. | |
| 5,661,774 A | 8/1997 | Gordon et al. | |
| 6,091,795 A | 7/2000 | Schafer et al. | |
| 6,323,492 B1 * | 11/2001 | Clinthorne ................... 250/394 |
| 6,754,298 B2 * | 6/2004 | Fessler ........................... 378/4 |
| 7,015,477 B2 * | 3/2006 | Gunter ........................ 250/369 |
| 7,085,405 B1 * | 8/2006 | Levkovitz et al. .......... 382/131 |
| 2004/0251418 A1 * | 12/2004 | Gunter ........................ 250/369 |

FOREIGN PATENT DOCUMENTS

DE 31 50 3 06 A1 6/1983

OTHER PUBLICATIONS

K. Chuang an H. K. Huang, A Fast Dual-Energy Computational Method Using Isotransmission Lines and Tables, Med. Phys. 14, 186-192 (1987).

H. N. Cardinal and A. Fenster, An Accurate Method for Direct Dual Energy Calibration and Decomposition, Med. Phys. 17, 327-341 (1990).

W. H. Press, S.A. Teukolsky, W. T. Vetterling and B.P. Flannery, Numerical Recipes in C, The Art of Scientific Computing, 2nd Ed. (Cambridge University Press, New York, NY 1992), Chap. 15, pp. 681-706.

* cited by examiner

*Primary Examiner*—Bhavesh M. Mehta
*Assistant Examiner*—Wes Tucker
(74) *Attorney, Agent, or Firm*—McDermott Will & Emery LLP

(57) ABSTRACT

A method of decomposition of projection data is provided, wherein such projection data includes input projection data acquired using at least two x-ray spectra for a scanned object, including low energy projection data ($P_L$) and high energy projection data ($P_H$); the method comprises solving the projections $P_L$ and $P_H$ to determine a photoelectric line integral ($A_p$) component of attenuation and a Compton line integral ($A_c$) component of attenuation of the scanned object using a multi-step fitting procedure and constructing a Compton image $I_c$ and a photoelectric image $I_p$ from the Compton line integral and photoelectric line integral.

47 Claims, 7 Drawing Sheets

DECOMPOSITION OF MULTI-ENERGY SCAN PROJECTIONS USING MULTI-STEP FITTING

CROSS REFERENCES TO RELATED APPLICATIONS

There are no prior related patent applications.

STATEMENT OF GOVERNMENT INTEREST

The U.S. Government has no interest in or to the present invention.

FIELD OF THE INVENTION

The present invention relates to systems and methods for detecting explosive materials using X-ray radiation transmission and scattering to determine one or more physical characteristics of a material, and more particularly, to systems and methods for performing decomposition of scan projections used in such systems and methods.

BACKGROUND

Various X-ray baggage scanning systems are known for detecting the presence of explosives and other prohibited items in baggage, or luggage, prior to loading the baggage onto a commercial aircraft. A common technique of measuring a material's density is to expose the material to X-rays and to measure the amount of radiation absorbed by the material, the absorption being indicative of the density. Since many explosive materials may be characterized by a range of densities differentiable from that of other items typically found in baggage, explosives are generally amenable to detection by X-ray equipment.

Most X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates an X-ray beam that passes through and is partially attenuated by the baggage and is then received by the detector array. During each measuring interval the detector array generates data representative of the integral of density of the planar segment of the baggage through which the X-ray beam passes, and this data is used to form one or more raster lines of a two-dimensional image. As the conveyor belt transports the baggage past the stationary source and detector array, the scanner generates a two-dimensional image representative of the density of the baggage, as viewed by the stationary detector array. The density image is typically displayed for analysis by a human operator.

Techniques using dual energy X-ray sources are known for providing additional information about a material's characteristics, beyond solely a density measurement. Techniques using dual energy X-ray sources involve measuring the X-ray absorption characteristics of a material for two different energy levels of X-rays. Depending upon the calibration of the scanner, dual energy measurements provide an indication of dual parameters of the material being scanned; for example, at one calibration setting, the dual parameters can be chosen to be the material's atomic number and the material's density. At another calibration setting, the dual parameters can be chosen to be the material's Photoelectric coefficients and the material's Compton coefficients. At yet another calibration setting, the dual parameters can be chosen to be an amount of a first material present (e.g., plastic) and an amount of a second material present (e.g., aluminum). Dual energy X-ray techniques for energy-selective reconstruction of X-ray Computer Tomography (hereinafter referred to as CT) images are described, for example, in Robert E. Alvarez and Albert Macovski, "Energy-selective Reconstructions in X-ray Computerized Tomography", Phys. Med. Biol. 1976, Vol. 21, No. 5, 733–744; and U.S. Pat. Nos. 4,029,963 and 5,132,998. One algorithm used to generate such dual parameters from dual energy X-ray projection data is known as the Alvarez/Macovski Algorithm (hereinafter referred to as AMA).

One proposed use for such dual energy techniques has been in connection with a baggage scanner for detecting the presence of explosives in baggage. Explosive materials are generally characterized by a known range of atomic numbers and are therefore amenable to detection by such dual energy X-ray sources. One such dual energy source is described in U.S. Pat. No. 5,661,774, entitled "Improved Dual Energy Power Supply."

Plastic explosives present a particular challenge to baggage scanning systems because, due to their moldable nature, plastic explosives may be formed into geometric shapes that are difficult to detect. Most explosives capable of significantly damaging an aircraft are sufficiently large in length, width, and height so as to be readily detectable by an X-ray scanner system regardless of the explosive's orientation within the baggage. However, a plastic explosive powerful enough to damage an aircraft may be formed into a relatively thin sheet that is extremely small in one dimension and is relatively large in the other two dimensions. The detection of plastic explosives may be difficult because it may be difficult to see the explosive material in the image, particularly when the material is disposed so that the thin sheet is perpendicular to the direction of the X-ray beam as the sheet passes through the system.

Thus, detection of suspected baggage requires very attentive operators. The requirement for such attentiveness can result in greater operator fatigue, and fatigue as well as any distractions can result in a suspected bag passing through the system undetected. Accordingly, a great deal of effort has been made to design a better baggage scanner. Such designs, for example, have been described in U.S. Pat. No. 4,759,047 (Donges et al.); U.S. Pat. No. 4,884,289 (Glockmann et al.); U.S. Pat. No. 5,132,988 (Tsutsui et al.); U.S. Pat. No. 5,182,764 (Peschmann et al.); U.S. Pat. No. 5,247,561 (Kotowski); U.S. Pat. No. 5,319,547 (Krug et al.); U.S. Pat. No. 5,367,552 (Peschmann et al.); U.S. Pat. No. 5,490,218 (Krug et al.) and German Offenlegungsschrift DE 31 503 06 A1 (Heimann GmbH).

At least one of these designs, described in U.S. Pat. No. 5,182,764 (Peschmann et al.) and U.S. Pat. No. 5,367,552 (Peschmann et al.) (hereinafter the '764 and '552 patents), has been commercially developed and is referred to hereinafter as the "Invision Machine." The Invision Machine includes a CT scanner of the third generation type, which typically includes an X-ray source and an X-ray detector system secured respectively to diametrically opposite sides of an annular-shaped platform or disk. The disk is rotatably mounted within a gantry support so that in operation the disk continuously rotates about a rotation axis while X-rays pass from the source through an object positioned within the opening of the disk to the detector system.

The detector system can include a linear array of detectors disposed as a single row in the shape of a circular arc having a center of curvature at the focal spot of the X-ray source, i.e., the point within the X-ray source from which the X-rays emanate. The X-ray source generates a fan shaped beam, or fan beam, of X-rays that emanates from the focal spot, passes through a planar imaging field, and is received by the detectors. The CT scanner includes a coordinate system defined by X-, Y- and Z-axes, wherein the axes intersect and are all normal to one another at the center of rotation of the disk as the disk rotates about the rotation axis. This center of rotation is commonly referred to as the "isocenter." The Z-axis is defined by the rotation axis and the X- and Y-axes are defined by and lie within the planar imaging field. The fan beam is thus defined as the volume of space defined between a point source, i.e., the focal spot, and the receiving surfaces of the detectors of the detector array exposed to the X-ray beam. Because the dimension of the receiving surfaces of the linear array of detectors is relatively small in the Z-axis direction the fan beam is designed to be relatively thin in the Z-axis direction. Each detector generates an output signal representative of the intensity of the X-rays incident on that detector. Since the X-rays are partially attenuated by all the mass in their path, the output signal generated by each detector is representative of the density of all the mass disposed in the imaging field between the X-ray source and that detector.

As the disk rotates, the detector array is periodically sampled, and for each measuring interval each of the detectors in the detector array generates an output signal representative of the density of a portion of the object being scanned during that interval. The collection of all of the output signals generated by all the detectors in a single row of the detector array for any measuring interval is referred to as a "projection," or equivalently as a "view," and the angular orientation of the disk (and the corresponding angular orientations of the X-ray source and the detector array) during generation of a projection is referred to as the "projection angle." At each projection angle, the path of the X-rays from the focal spot to each detector, called a "ray," increases in cross section from a point source to the receiving surface area of the detector, and thus is thought to magnify the density measurement because the receiving surface area of the detector area is larger than any cross sectional area of the object through which the ray passes.

As the disk rotates around the object being scanned, the scanner generates a plurality of projections at a corresponding plurality of projection angles. Using well known algorithms a CT image of the object may be generated from all the projection data collected at each of the projection angles. The CT image is representative of the density of a two dimensional "slice" of the object through which the fan beam has passed during the rotation of the disk through the various projection angles. The resolution of the CT image is determined in part by the width of the receiving surface area of each detector in the plane of the fan beam, the width of the detector being defined herein as the dimension measured in the same direction as the width of the fan beam, while the length of the detector is defined herein as the dimension measured in a direction normal to the fan beam parallel to the rotation or Z-axis of the scanner. In general, the resolution of the CT image is inversely proportional to the width of the receiving surface of each detector in the plane of the fan beam.

FIGS. 1, 2 and 3 show perspective, end cross-sectional and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 can be a two-dimensional array such as the array described in U.S. Pat. No. 6,091,795 entitled, "Area Detector Array for Computed Tomography Scanning System." The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidically shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles.

Pre-reconstruction analysis, post-reconstruction analysis and multiple projection/non-CT analysis are three prior art techniques generally recognized for using dual energy X-ray sources in materials analysis (e.g., in a baggage scanner for detecting the presence of explosives in baggage). In pre-reconstruction analysis, the signal flow is as shown in FIG. 4. The scanner 120 is typically similar to the one shown in FIG. 1 and has an X-ray source capable of producing a fan beam at two distinct energy levels (i.e., dual energy). The DAS 134 gathers signals generated by detector array 130 at discrete angular positions of the rotating platform 124, and passes the signals to the pre-processing element 206. The pre-processing element 206 re-sorts the data it receives from the DAS 134 in order to optimize the sequence for the subsequent mathematical processing. The pre-processing element 206 also corrects the data from the DAS 134 for detector temperature, intensity of the primary beam, gain and offset, and other deterministic error factors. Finally, the pre-processing element 206 extracts data corresponding to high-energy views and routes it to a high energy channel path 208, and routes the data corresponding to low-energy views to a low energy path 210.

The projection computer 212 receives the projection data on the high energy path 208 and the low energy path 210 and performs Alvarez/Macovski Algorithm processing to produce a first stream of projection data 214 which is dependent on a first parameter of the material being scanned and a second stream of projection data 216 which is dependent on a second parameter of the material scanned. The first parameter is often the atomic number and the second parameter is often material density, although other parameters may be selected. A first reconstruction computer 218 receives the first stream of projection data 214 and generates a CT image from the series of projections corresponding to the first material parameter. A second reconstruction computer 220 receives the second stream of projection data 216 and generates a CT image from the series projections corresponding to the second material parameter.

In post-reconstruction analysis, the signal flow is as shown in FIG. 5. As is described herein for pre-processing analysis, a pre-processing element 206 receives data from a DAS 134, performs several operations upon the data, then routes the data corresponding to high-energy views to a high energy path 208 and routes the data corresponding to low-energy views to a low energy path 210. A first reconstruction computer 218 receives the projection data from the high-energy path 208 and generates a CT image corresponding to the high-energy series of projections. A second reconstruction computer 220 receives the projection data from the low-energy path 210 and generates a CT image corresponding to the low-energy series of projections. A projection computer 212 receives the high energy CT data 222 and the low-energy CT data 224 and performs AMA processing to produce CT data 226 which is dependent on a first parameter of the material being scanned and a second stream of projection data 228 which is dependent on a second parameter of the material scanned.

Various approaches have been used for decomposition of projection data (P). For example, the AMA non-linear equation approximates the integral equations by a second order power series in $A_c$ and $A_p$, where $A_c$ represents the Compton line integral and $A_p$ represents the Photoelectric line integral. The line integral equations are given as:

$$P_L = b_0 + b_1 A_c + b_2 A_p + b_3 A_c A_p + b_4 A_c^2 + b_5 A_p^2$$

$$P_H = c_0 + c_1 A_c + c_2 A_p + c_3 A_c A_p + c_4 A_c^2 + c_5 A_p^2 \quad (1)$$

The coefficients $b_i$ and $c_i$ are determined through a calibration procedure as follows. By measuring the projections values of the combination of various thickness of two known materials, a set of equations in the form of Equation 1 can be formed. Since $P_L$, $P_H$, $A_c$ and $A_p$ are known for the calibration data, the coefficients are calculated using a polynomial least squares fitting algorithm.

Once the coefficients $b_i$ and $c_i$ are determined, the decomposition of the Compton ($A_c$) and Photoelectric ($A_p$) images from projections $P_L$, $P_H$ is accomplished by solving Equation 1 using the Newton-Raphson method for each pixel in the image.

The disadvantage of the method is that it is computationally slow and potentially unstable because the iteration can diverge if the initial guess to the solution of Equation 1 is not sufficiently close to the true solution. Therefore, the method is susceptible to noise and to extrapolation outside the region of calibration causing large approximation errors.

Another prior art method of performing decomposition is the direct approximation method, discussed in L. A. Lehmann, R. E. Alvarez, A. Macovski, W. R. Brody, N. J. Pelc, S. J. Riederer, and A. L. Hall, *Generalized Image Combinations In Dual KVP Digital Radiography*, Med. Phys. 8, 659–667 (1981). In the direct approximation method, $A_c$ and $A_p$ are expressed as a power series in $P_L$, $P_H$ $$A_c = d_0 + d_1 P_L + d_2 P_H + d_3 P_L P_H + d_4 P_L^2 + d_5 P_H^2$$

$$A_p = e_0 + e_1 P_L + e_2 P_H + e_3 P_L P_H + e_4 P_L^2 + e_5 P_H^2 \quad (2)$$

As in the non-linear equation method, the coefficients $d_i$ and $e_i$ are determined through a calibration procedure, as follows. By measuring the projections values of the combination of various thicknesses of two known materials, one obtains a set of equations in the form of Equation 1. Since $P_L$, $P_H$, $A_c$ and $A_p$ are known for the calibration data, the coefficients are calculated using a polynomial least squares fitting algorithm. For a given pair of projections ($P_L$, $P_H$), $A_c$ and $A_p$ are can be calculated directly from Equation 2.

The direct decomposition method avoids the issues of iterative convergence of the non-linear equations. However, the method has the disadvantage that it requires a large number of polynomial terms in Equation 2 in order to obtain accuracy over an extended range of projection values. The use of higher order polynomials then introduces a ripple which can be controlled only by obtaining a large number of calibration points.

In yet another prior art method, decomposition is accomplished using iso-transmission lines, described K. Chuang and H. K. Huang, *A Fast Dual-Energy Computational Method Using Isotransmission Lines and Tables*, Med. Phys. 14, 186–192 (1987). According to this method, for a given projection value, an iso-transmission line is represented by a linear equation in two basis functions, wherein the thickness of aluminum and plastic (as examples) is given by $t_{Al}$ and $t_{Pl}$, respectively, as:

$$P_L = a t_{Al} + b t_{Pl}$$

$$P_H = d t_{Al} + e t_{Pl} \quad (3)$$

where $P_L$ and $P_H$ are the high and low energy projections and a, b, d, e are regression coefficients that are proportional to the attenuation coefficients of aluminum and plastic. The solution of Equation 3 determines the aluminum and plastic combination ($t_{Al}$, $t_{Pl}$) that determines ($P_L$, $P_H$).

The regression coefficients are generated from high and low energy calibration tables. The tables contain regression coefficients generated for pre-defined projection values. The pre-defined projections are generated by scanning known thicknesses of aluminum and plastic. For a given projection value, the regression coefficients are generated by interpolation between the closest two pre-defined coefficients stored in the table.

The iso-transmission line method requires a large amount of calibration data in order to generate the regression coefficients a, b, d, e. Further, the iso-transmission lines become increasingly non-linear as the projection value increases. In such a situation, the linear equations are not valid and the method causes large approximation errors.

Other prior methods for dual energy decomposition also suffer from shortcomings, as discussed in H. N. Cardinal and A, Fenster, *An Accurate Method For Direct Dual Energy Calibration and Decomposition* by, Med. Phys. 17, 327–341 (1990). As an example, the direct decomposition algorithm produces incomplete separation of objects, as determined visually. Additionally, the direct decomposition algorithm also introduces artifacts in the decomposed images of scanner data. The artifacts are primarily produced by approximation errors, sensitivity to noise and the lack of handling of exceptions in the input projection data. In addition, the algorithm requires a calibration procedure that is complicated, time consuming and prone to measurement errors, which propagate through the decomposition procedure to be manifested as artifacts in images.

SUMMARY OF THE INVENTION

In accordance with the present invention, a dual energy decomposition algorithm with multi-step fitting is provided that better separates objects with fewer artifacts and produces fewer false alarms. In accordance with the present invention the dual energy decomposition algorithm may be comprised of two sub-processes or parts (or sub-algorithms). First, the decomposition algorithm that operates on received or detected scanner data. Second, if not yet performed, prior to performing the decomposition, a calibration procedure may be performed to calibrate the decomposition algorithm. Accordingly, below, the dual energy decomposition algorithm is discussed and the optional calibration procedure is also discussed. Generally speaking, these two sub-process execute independently, at different times, so are discussed separately.

The calibration procedure can use simulated data or measured data or a combination of simulated and measured data. Using simulated data or stored measured data allows the calibration procedure to be relatively quick to perform and free from noise. Preferably, such a calibration procedure is not machine-specific and can be done once per scanner design. In still other embodiments, a noise reduction module or step may be included prior to processing projection data using the dual energy decomposition algorithm.

Dual energy decomposition with multi-step fitting in accordance with the present invention is useful for the decomposition of projection data, wherein such projection data may include input projection data acquired using at least two x-ray spectra for a scanned object, including low energy projection data ($P_L$) and high energy projection data ($P_H$). The method comprises solving the projections $P_L$ and $P_H$ to determine a photoelectric line integral ($A_p$) component of attenuation and a Compton line integral ($A_c$) component of attenuation of the scanned object using a multi-step fitting procedure and reconstructing a Compton image $I_c$ and a photoelectric image $I_p$ from the Compton line integral and photoelectric line integral.

The method may further include, prior to solving the projections, performing a calibration procedure using simulated data, wherein the calibration procedure may include generating low energy iso-transmission contours for known values of $P_L$ at known values of the photoelectric line integral $A_p$ and at known values of the Compton line integral $A_c$. According to the method, for each low-energy iso-transmission contour corresponding to PL, minimum and maximum values of $P_H$ may be computed, i.e., $P_{H\_min}$ and $P_{H\_max}$. A polynomial $m_L$ may be used to determine a minimum bound on $P_H$, and the multi-step fitting procedure may further include a fitting procedure for fitting the minimum values of $P_H$ to a polynomial function $m_L(P_L)$. Also, the method may further include using a polynomial $n_L$ to determine a maximum bound on $P_H$, and the multi-step fitting procedure may include a fitting procedure for fitting the maximum values of $P_H$ to a polynomial function $n_L(P_L)$.

The multi-step fitting procedure may include a fitting procedure wherein, for each of the low energy iso-transmission contours, $A_p$ is fit to a polynomial function $g_L(A_c)$. And, the calibration procedure may further include fitting the set of coefficients $g_{Li}$ determined for known values of $P_L$ to a polynomial function $h_{Li}(P_L)$.

The calibration procedure may also include generating high energy iso-transmission contours for known values of $P_H$ at known values of $A_p$ and at known values of $A_c$. The multi-step fitting procedure may then include for each of the high energy iso-transmission contours, fitting $A_p$ to a polynomial function of $g_H(A_c)$. And, the calibration procedure may further include fitting the set of coefficients $g_{Hi}$ determined for known values of $P_H$ to a polynomial function $h_{Hi}(P_H)$.

Apart from calibration, the dual energy decomposition procedure with multi-step fitting method may also include generating a low energy iso-transmission contour corresponding to $P_L$ and a high energy iso-transmission contour corresponding to $P_H$. The method may then include determining the values of the photoelectric line integral $A_p$ and Compton line integral $A_c$ at the intersection of the low energy iso-transmission contour and the high energy iso-transmission contour, wherein the intersection of the low energy iso-transmission contour and the high energy iso-transmission contour may be determined by equating a first polynomial function representing the low energy iso-transmission contour with a second polynomial function representing the high energy iso-transmission contour. In such a case, the coefficients of the first polynomial function may be determined using $P_L$ and the polynomial function $h_L(P_L)$ generated during calibration, and wherein the coefficients of the second polynomial function may be determined using $P_H$ and the polynomial function $h_H(P_H)$ generated during calibration.

The method may include computing a modified value of the input low energy projection data and a modified value of the input high energy projection data, wherein each of the modified values, designated as $P_{Lc}$ for low energy projection data and $P_{Hc}$ for high energy projection data, is clamped to be bounded between two values. The coefficients of the low energy iso-transmission contour may be computed for the value of PLC using the polynomial function $h_L$ generated during calibration, as described above, wherein $h_L$ describes the variation of the coefficients of the polynomial $g_L$, which describes the shape of the low energy iso-transmission contour for the value of $P_{Lc}$. The coefficients of the high energy iso-transmission contour may be computed for the value of $P_{Hc}$ using the polynomial function $h_H$ generated during calibration, as described above, wherein $h_H$ describes the variation of the coefficients of the polynomial $g_H$, which describes the shape of the high energy iso-transmission contour for the value of $P_{Hc}$. The modified value $P_{Lc}$ is computed by clamping the value of $P_L$ to lie between 0 and the maximum value of $P_L$ used to generate the calibration data. In accordance with the method, the modified value $P_{Hc}$ may be determined by clamping the value of $P_H$ to lie between a minimum value of $P_H$ (i.e., $P_H^{min}$) and a maximum value of $P_H$ (i.e, $P_H^{max}$). $P_H^{min}$ and $P_H^{max}$ are determined using the polynomials $m_L$ and $n_L$, determined during calibration, and as a function of $P_{Lc}$, wherein $m_L$ is a polynomial used to determine $P_H^{min}$ and $n_L$ is a polynomial used to determine $P_H^{max}$.

The method may also include calculating a scaled Compton line integral value ($A_{cs}$) as a function of a scale factor $s_c$ and $A_c$ and calculating a scaled photoelectric line integral value ($A_{ps}$) as a function of a scale factor $s_p$ and $A_{ps}$. Scaling $A_c$ and $A_p$ is performed to obtain pixel intensities within a specific range of values if $A_c$ and $A_p$ are reconstructed into images. The method may further include reconstructing image $I_c$ and image $I_p$ as a function of $A_{cs}$ and $A_{ps}$. The method may then include determining an image of a basis function $X(I_X)$ and said basis function $Y(I_Y)$, by solving image $I_c$ and image $I_p$ on a pixel-by-pixel basis. The basis functions are two functions that can be combined to determine the pixel intensities in the Compton image and a photoelectric image $I_p$.

A system for decomposing projection data using multi-step fitting that includes modules configured to implement the above functionality may also be provided. Such a system may include, for projection data of a set of scanned objects acquired using at least two x-ray spectra, media for storing low energy projection data (PL) and high energy projection data ($P_H$). The system may include a calibration module configured to calibrate the decomposition module using at least some simulated data; generate a low energy iso-transmission contour corresponding to known values of $P_L$ and a high energy iso-transmission contour corresponding to known values of $P_H$; generate a polynomial $g_L$ that represents the shape of the low energy iso-transmission contour; and generate a polynomial $g_H$ that represents the shape of the high energy iso-transmission contour; generate polynomials $h_L$ that represent the variation of the coefficients of the polynomial $g_L$ as a function of $P_L$; generating polynomial $h_H$ that represents the variation of the coefficients of the polynomial $g_H$ as a function of $P_H$; and determining the minimum and maximum values of $P_H$ for each transmission line corresponding each $P_L$; and generating a polynomial $m_H$ that represents the variation of the minimum value of $P_H$ as a function of $P_L$; and generating a polynomial $n_H$ that represents the variation of the maximum value of $P_H$ as a function of $P_L$;

A decomposition module may be provided that is configured to determine a photoelectric line integral ($A_p$) component of attenuation and a Compton line integral ($A_c$) component of attenuation for measured values of $P_L$ and $P_H$ using multi-step fitting, and configured to determine coefficients of $g_L$ using $P_L$ and $h_L(P_L)$ and determine coefficients of $g_H$ using $P_H$ and $h_H(P_H)$ wherein $A_c$ and $A_p$ are determined as a function of $P_L$ and $P_H$ using the coefficients of $g_L$ and the coefficients of $g_H$.

The system may also include an image reconstruction module configured to reconstruct a Compton image ($I_c$) and a photoelectric image ($I_p$) from the $A_p$ and $A_c$. The image reconstruction module may be configured to determine an image of a basis function $X(I_X)$ and of a basis function $Y(I_Y)$, by solving image $I_c$ and image $I_p$ on a pixel-by-pixel basis.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

Figure 1:
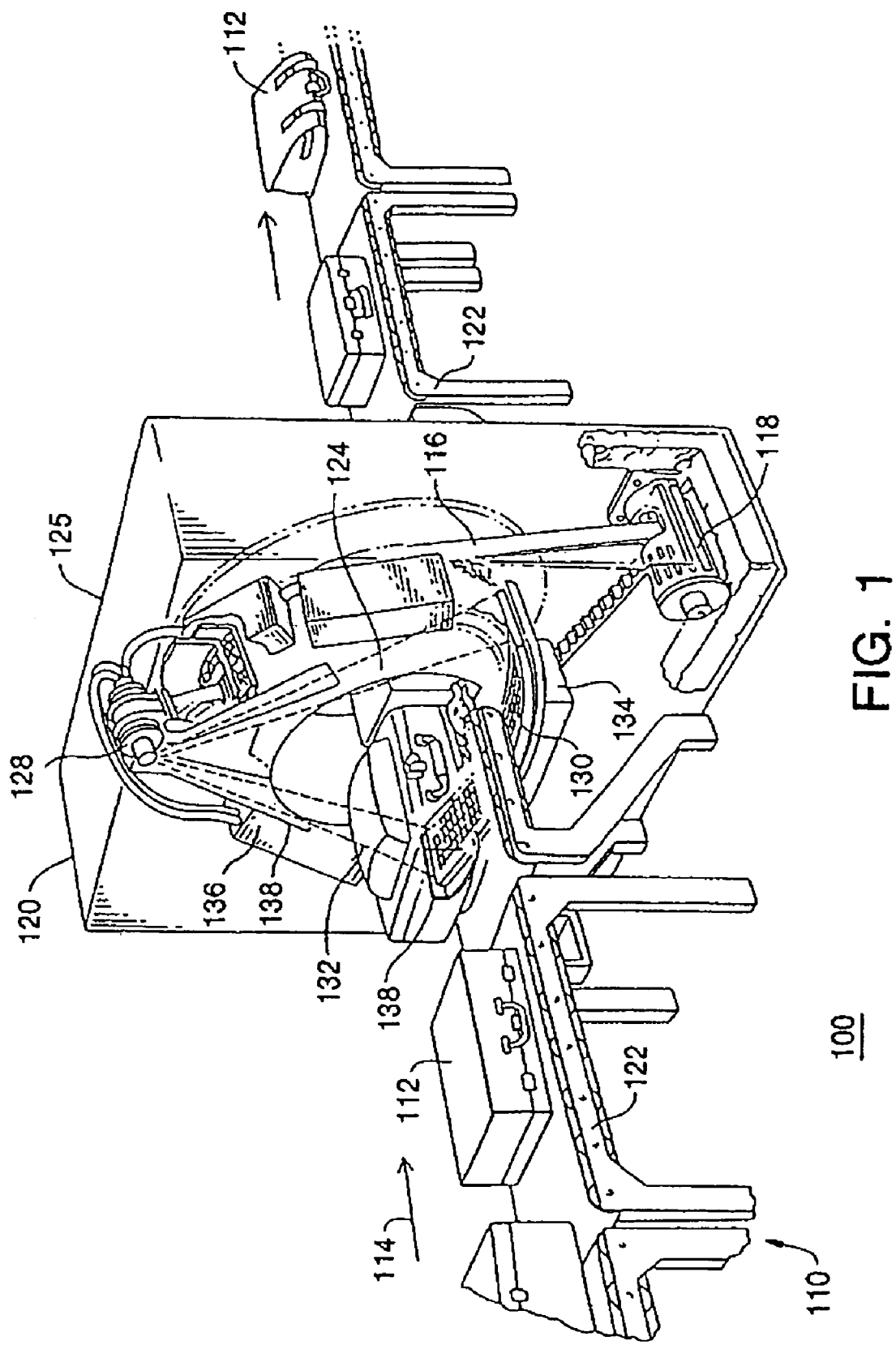
FIG. 1 is a perspective view of a baggage scanning system, known in the prior art.

In accordance with the present invention, a dual energy decomposition algorithm is provided that better separates objects with fewer artifacts and produces fewer false alarms, and preferably uses at least a two step fitting process, generally referred to as "dual energy decomposition with multi-step fitting". A decomposition algorithm in accordance with the present invention may also use a calibration procedure that is based at least in part, if not entirely, on simulated data, and therefore is quick to perform and free from noise often introduced by other forms of calibration data. The calibration procedure may also be performed using measured data or a combination of simulated data and measured data. Preferably, such a calibration procedure is not machine-specific and can be done once per scanner design. In still other embodiments, a noise reduction module or step may be included prior to processing of projection data. Given that the calibration procedure and the dual energy decomposition algorithm operate relatively independently, they are generally discussed below separately.

For the range of photon energies used for medical and commercial diagnostic imaging (i.e., from about 20 to 200 keV), the attenuation of an object is determined by the photoelectric absorption and Compton scatter. Photoelectric absorption consists of an x-ray photon imparting all of its energy to a tightly bound inner electron in an atom. The electron uses some of its acquired energy to overcome the binding energy within its shell, the rest appearing as kinetic energy of the thus freed electron. Compton scatter consists of the interaction of the x-ray photon with either a free electron, or one that is loosely bound in one of the outer shells of an atom. As a result of Compton scatter, the x-ray photon is deflected from its original direction of travel with some loss of energy, which is gained by the electron. Both the photoelectric and Compton effects are energy dependent.

The linear attenuation coefficient, $\mu(x,y,E)$ for a given material as a function of energy E and spatial position (x,y) in a plane can be approximated as:

$$\mu(x,y,E) = a_p(x,y)\Phi_p(E) + a_c(x,y)\Phi_c(E) \quad (4)$$

where $\Phi_p(E)$ is the photoelectric energy dependence given by:

$$\Phi_p(E) = \frac{1}{E^{3.2}} \quad (5)$$

and $\Phi_c(E)$ is the Compton energy dependence that is described by the Klein-Nishina function given by:

$$\Phi_c(E) = \frac{1+\alpha}{\alpha}\left[\frac{2(1+\alpha)}{(1+2\alpha)} - \frac{1}{\alpha}\ln(1+2\alpha)\right] + \frac{1}{2\alpha}\ln(1+2\alpha) - \frac{(1+3\alpha)}{(1+2\alpha)^2} \quad (6)$$

where $\alpha = E/510.975$ keV. The parameters $a_p(x,y)$ and $a_c(x,y)$ are constants that depend on the material composition, namely:

$$a_p(x,y) = \rho_e(x,y)BZ^n(x,y)$$

$$a_c(x,y) = \rho_e(x,y) \quad (7)$$

where $B = 9.8 \times 10^{-24}$ is a constant, $n \approx 3$, $Z(x,y)$ is the atomic number, and $\rho_e(x,y)$ is the electron density given by:

$$\rho_e(x,y) = N_A\left(\frac{Z(x,y)}{W(x,y)}\right) \quad (8)$$

where $N_A$ is Avogadro's number ($6.023 \times 10^{23}$) and $W(x,y)$ is the atomic weight.

In accordance with the present invention, the Compton coefficient, $a_c(x,y)$, and the photoelectric coefficient, $a_p(x,y)$, of an unknown material may be determined on a per-pixel basis from images reconstructed from projection measurements using at least two source spectra, i.e., low energy and high energy. A dual energy decomposition algorithm with multi-step fitting, in accordance with the present invention, comprises the following steps, described in greater detail below:

1) The projections of the objects are measured using at least two different source spectra, obtained by varying voltage to the x-ray tube and optionally changing the beam filtration.

2) The projections (P) are decomposed into line integrals of the photoelectric and Compton components of attenuation using a two-step fitting procedure.

3) The photoelectric and Compton line integrals are filtered and "back projected" to reconstruct photoelectric and Compton images.

4) Optionally, the photoelectric and Compton images are solved on a pixel-by-pixel basis to generate images of two known basis functions, such as aluminum and plastic, as one example, or mass and atomic number, as another example.

Figure 6:
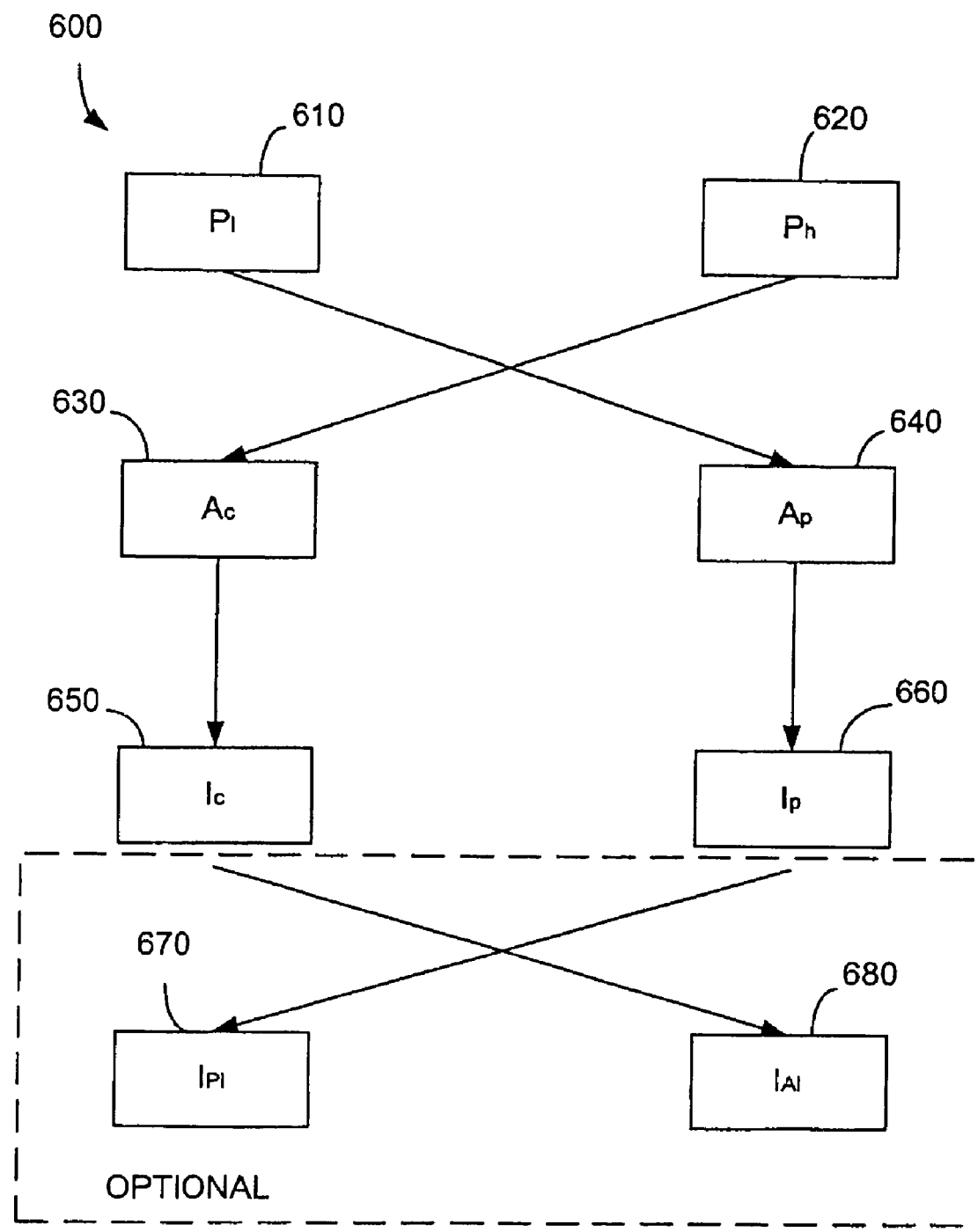
FIG. 6 is a flowchart showing a method of dual energy decomposition with multi-step fitting, in accordance with the present invention.

FIG. 6 is a flow chart 600 showing the above steps of dual energy decomposition in accordance with the present invention. Input projections $P_L$ 610 (low energy) and $P_H$ 620 (high energy) are decomposed into Compton and photoelectric line integrals, $A_c$ 630 and $A_p$ 640, respectively. $A_c$ and $A_p$ are back-projected to generate the Compton and Photoelectric images $I_c$ 650 and $I_p$ 660. $I_c$ and $I_p$ are optionally solved to determine the images of the basis functions, e.g., for plastic and aluminum, $I_{Pl}$ 670 and $I_{Al}$ 680. "Solving" the images is a mathematical operation described in more detail below.

I: Overview of Decomposition with Multi-Step Fitting

Figure 2:
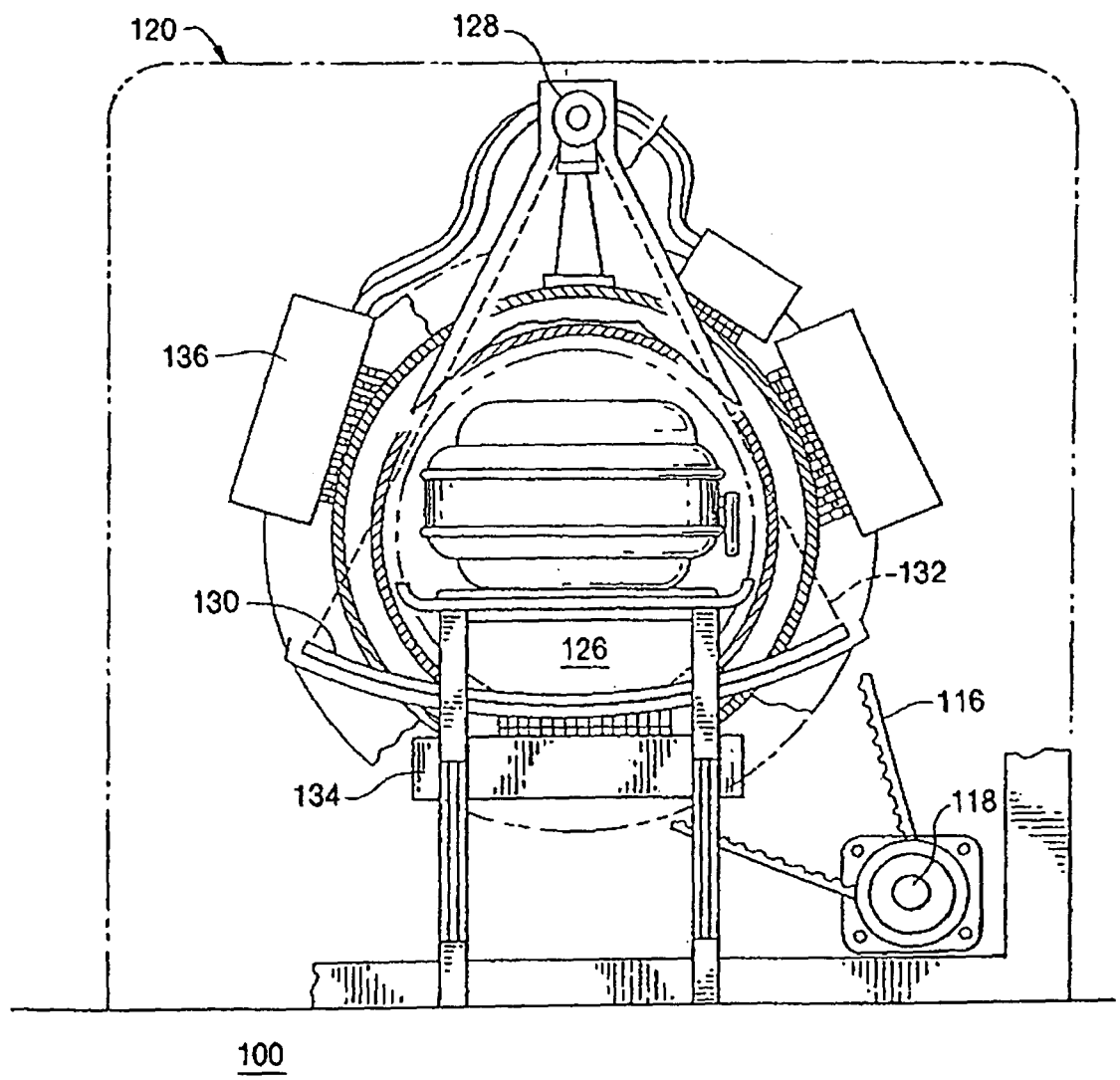
FIG. 2 is a cross-sectional end view of the system of FIG. 1.
Figure 3:
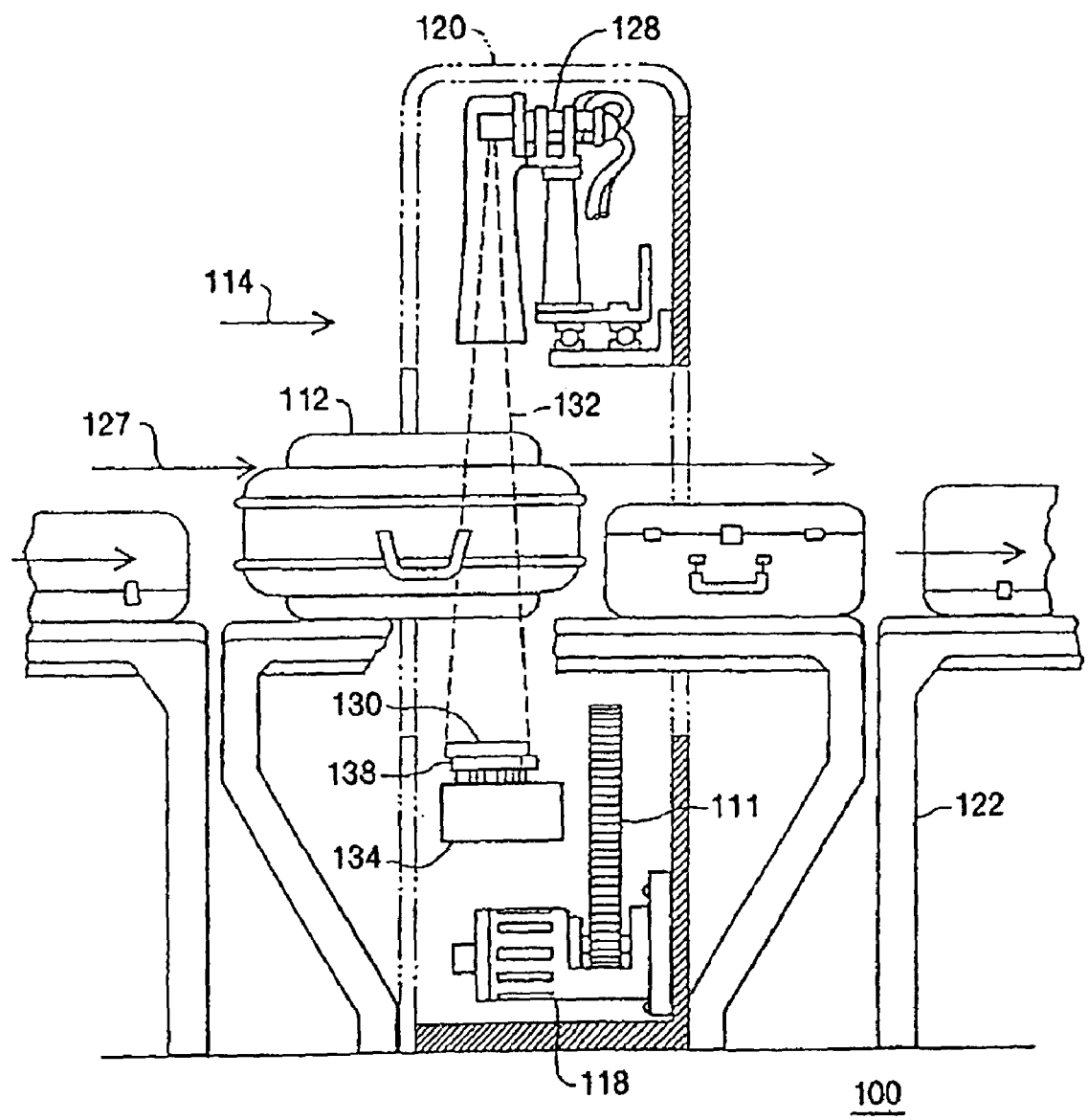
FIG. 3 is a cross-sectional radial view of the system of FIG. 1.
Figure 4:
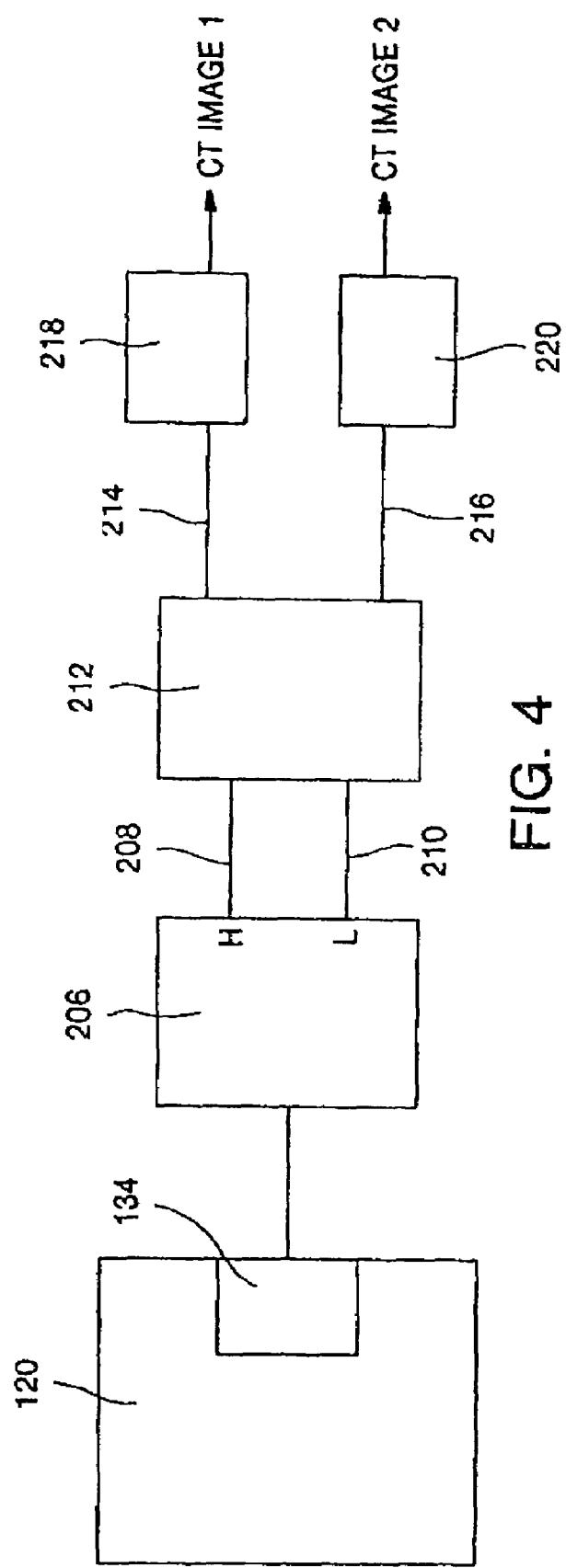
FIG. 4 is a signal flow diagram of a system capable of performing pre-construction analysis, useful in the system of FIG. 1.
Figure 5:
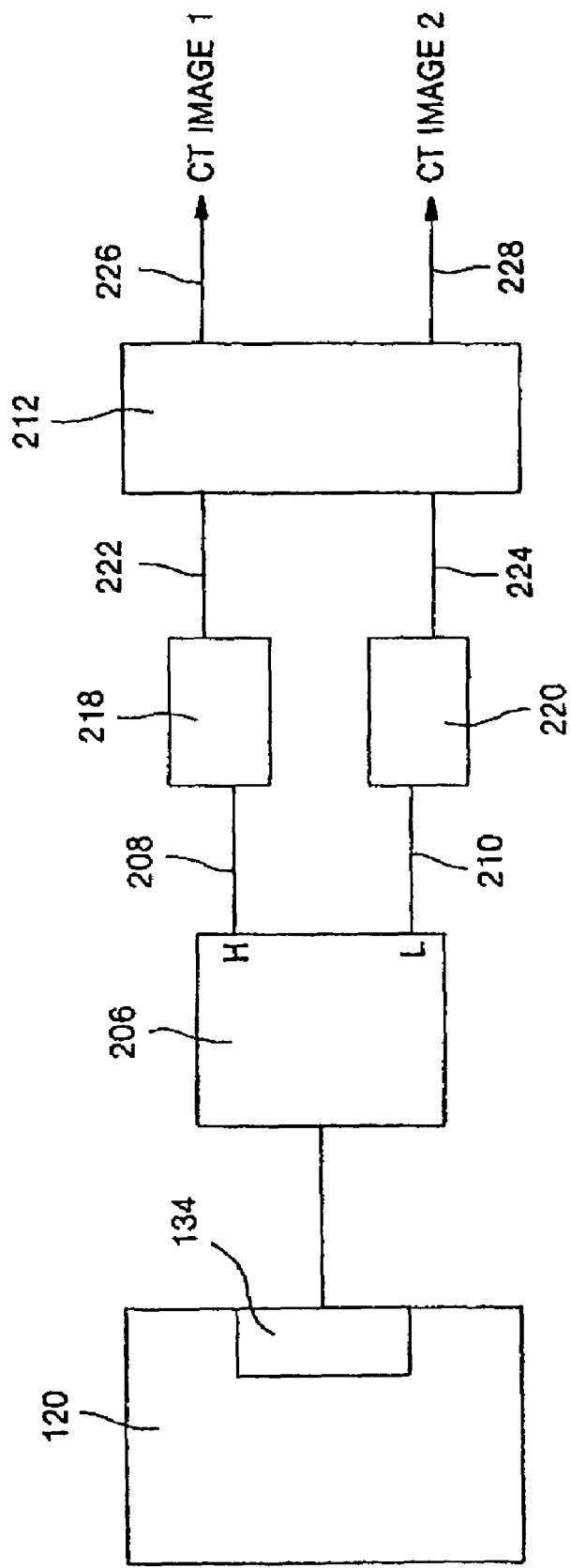
FIG. 5 is a signal flow diagram of a system, like that of FIG. 1, capable of performing post-reconstruction analysis.

An overview of the mathematics of present dual energy decomposition with multi-step fitting is provided below. This embodiment, which is also applicable to three-dimensional data, is described with respect to a CT scanner with an x-ray source and detector configuration, such as that shown and described with respect to FIGS. 1, 2, and 3. For this example, an object with attenuation $\mu(x,y,E)$ is scanned. An example of one such scanner is the AN6000 EDS scanner by Analogic Corporation, Peabody, Mass. The scanner source generates a low energy spectrum $S_L$ and a high energy spectrum $S_H$. $I_L$ and $I_H$ are the corresponding x-ray intensities that are detected when the object is scanned, given by:

$$I_L = \int_0^\infty S_L(E) e^{-\int \mu(x,y,E)ds} dE$$

$$I_H = \int_0^\infty S_H(E) e^{-\int \mu(x,y,E)ds} dE \quad (9)$$

$I_{oL}$ and $I_{oH}$ are the corresponding x-ray intensities that are detected in the absence of any object, given by:

$$I_{oL} = \int_0^\infty S_L(E) dE$$

$$I_{oH} = \int_0^\infty S_L(E) dE \quad (10)$$

and $\int \mu(x,y,E)ds$ is the path integral, which represents the attenuation of x-rays as they travel along a straight line through the object.

$P_L$ and $P_H$ are the corresponding low and high energy projections that are measured by the scanner's detector, given by:

$$P_L = -\ln\left(\frac{I_L}{I_{oL}}\right) = -\ln\int_0^\infty S_L(E) e^{-\int \mu(x,y,E)ds} dE + \ln \int S_L(E) dE \quad (11)$$

$$P_H = -\ln\left(\frac{I_H}{I_{oH}}\right) = -\ln\int_0^\infty S_H(E) e^{-\int \mu(x,y,E)ds} dE + \ln \int S_H(E) dE$$

From Equation 4 for $\mu(x,y,E)$, the line integral $\int \mu(x,y,E)ds$ can be written as:

$$\int \mu(x,y,E)ds = A_p \Phi_p(E) + A_c \Phi_c(E) \quad (12)$$

where $A_c$ and $A_p$ are the line integrals of $a_c(x,y)$ and $a_p(x,y)$ given by:

$$A_c = \int a_c(x,y) ds$$

$$A_p = \int a_p(x,y) ds \quad (13)$$

Substituting Equation 12 into Equation 11 yields:

$$P_L = f_L(A_c, A_p) = -\ln \int S_L(E) e^{-A_p \Phi_p(E) - A_c \Phi_c(E)} dE + \ln \int S_L(E) dE$$

$$P_H = f_H(A_c, A_p) = -\ln \int S_H(E) e^{-A_p \Phi_p(E) - A_c \Phi_c(E)} dE + \ln \int S_H(E) dE \quad (14)$$

Equation 14 can then be solved to determine the values $(A_c, A_p)$ that generate the projections $(P_L, P_H)$ provided that the Jacobian (J), given by:

$$J = \det\begin{pmatrix} \frac{\partial P_L}{\partial A_c} & \frac{\partial P_L}{\partial A_p} \\ \frac{\partial P_H}{\partial A_c} & \frac{\partial P_H}{\partial A_p} \end{pmatrix} \quad (15)$$

is non-zero, where det represents the determinant.

Note that the direct analytical solution of Equation 14 is difficult to obtain because the exact analytic forms of the spectra, $S_L$ and $S_H$, are not easily measured. Therefore, several methods are described in the prior art to determine the solution of Equation 14 without knowledge of the spectra such as the direct decomposition method or the iso-transmission method, previously discussed. According to the present algorithm for dual energy decomposition with multi-step fitting, the solution of Equation 14 is preferably determined using the iso-transmission method.

Accordingly, the iso-transmission method used in the preferred embodiment, a given projection value $P_L$ can be determined by multiple values of $(A_c, A_p)$. The values lie on a contour, which is defined as an iso-transmission contour. Each contour is described by the equation:

$$A_p = g_L(A_c)|_{P_L} \quad (16)$$

where $g_L$ is a polynomial function that describes the shape of the contour for a given $P_L$ given by:

$$g_L(A_c)|_{P_L} + g_{L0} + g_{L1}A_c + g_{L2}A_c^2 + \ldots \quad (17)$$

where $g_{L_i}$ is the polynomial coefficient of order i for a given value of $P_L$.

Note that the polynomial must satisfy the following properties of the contour. The values of $A_c$ and $A_p$ are greater than or equal to zero and, therefore, lie in the first quadrant of a two dimensional coordinate system. The value of $A_p$ decreases as the value of $A_c$ increases. Therefore, for a given $A_c$, there is only one value of $A_p$ that determines $P_L$. Therefore, $g_L$ is a monotonically decreasing function within the first quadrant and is bounded the values $(A_{c\_max}, 0)$ and $(0, A_{p\_max})$ where $A_{c\_max}$ is the solution of the equation:

$$g_L(A_{c\_max})|_{P_L} = 0 \quad (18)$$

and $A_{p\_max}$ is determined as:

$$A_{p\_max} = g_L(0)|_{P_L} \quad (19)$$

The value of $P_H$ varies continuously along the contour according to the equation:

$$P_H|_{P_L} = f_H(A_c, g_L(A_c)|_{P_L}) \quad (20)$$

where $f_H$ is given by Equation 14. Since $g_L$ is a monotonically decreasing function within the first quadrant, $P_H$ must lie between the following maximum and minimum values, given by:

$$P_H^{min}|_{P_L} = f_H(A_{c\_max}, 0)$$

$$P_H^{max}|_{P_L} = f_H(0, A_{p\_max}) \quad (21)$$

For a given $P_H$, the iso-transmission contour is described by the equation:

$$A_p = g_H(A_c)|_{P_H} \quad (22)$$

where $g_H$ is a polynomial function that describes the shape of the contour for a given $P_H$, given by:

$$g_H(A_c)|_{P_H} = g_{H0} + g_{H1}A_c + g_{H2}A_c^2 + \ldots \quad (23)$$

where $g_{Hi}$ is the polynomial coefficient of order i for a given value of $P_H$.

In the preferred form, a calibration procedure is used to determine the coefficients of $g_L$ and $g_H$ for arbitrary projection values. The calibration steps used for the determination of $g_L$ are as follows. An iso-transmission contour is generated for a known value of $P_L$ using known values of $(A_c, A_p)$ and simulated high and low energy spectra. The function $g_L$ is fit to the iso-transmission contour to determine the coefficients of $g_L$ for the value of $P_L$. The coefficients $g_{Li}$ are generated using the above procedure for several known values of $P_L$ up to a maximum value of $P_{L\_max}$. The variation of each coefficient with projection value is fit to a polynomial function $h_L$ given by:

$$g_{Li} = h_{Li0} + h_{Li1}P_L + h_{Li2}P_L^2 + \ldots \quad (24)$$

where $h_{Lij}$ is the polynomial coefficient of order j (0, 1, 2 . . . ) that determine the coefficient $g_{Li}$. The function $h_L$ is used to compute the coefficients of $g_{Li}$ for any value of $P_L$. The above procedure is repeated to generate the coefficients of the polynomial function $h_H$, which is used to compute the coefficients of $g_H$ for any value of $P_H$.

Additionally, the variation of the minimum and maximum values of $P_H$ for each iso-transmission contour are fit to polynomial functions given by:

$$P_H^{min}|_{P_L} = m_{L0} + m_{L1}P_L + m_{L2}P_L^2 + \ldots$$

$$P_H^{max}|_{P_L} = n_{L0} + n_{L1}P_L + n_{L2}P_L^2 + \ldots \quad (25)$$

Once the polynomials $g_L$ and $g_H$ are determined for the projections $(P_L, P_H)$, the solution of Equation 14 are determined by the coordinates of the point of intersection of the two contours determined by Equations 17 and 22 as:

$$g_L(A_c)|_{P_L} = g_H(A_c)|_{P_H} \quad (26)$$

provided that the values $(P_L, P_H)$ satisfy the conditions:

$$0 \leq P_L \leq P_L^{max}$$

$$P_H^{min}|_{P_L} \leq P_H \leq P_H^{max}|_{P_L} \quad (27)$$

where $P_L^{max}$ is the maximum value of $P_L$ used in calibration, and $P_H^{min}|_{P_L}$ and $P_H^{max}|_{P_L}$ are determined using Equation 25.

Once the values of $(A_c, A_p)$ are determined for all projections, $(A_c, A_p)$ are back-projected to reconstruct a Compton image $I_c$ and a photoelectric image $I_p$. The intensity of a given pixel (x, y) in $I_c$ is the value $a_c(x, y)$. The intensity of a given pixel (x, y) in $I_p$ is the value $a_p(x, y)$.

As an optional step, the photoelectric and Compton images are then solved on a pixel-by-pixel basis to generate images of two known basis functions. Examples of basis functions are the amount of aluminum and plastic, or mass and atomic number. Continuing with the illustrative embodiment, the basis functions for aluminum and plastic are used. One reason for using aluminum and plastic for illustrative purposes is that the Compton and photoelectric coefficients of aluminum and plastic differ from each other significantly (see Table 1) and span a wide range of atomic numbers that are encountered in baggage scanning.

TABLE 1

Compton & photoelectric coefficients for aluminum and plastic

| Coefficient | Aluminum | Plastic | Units |
|---|---|---|---|
| $\alpha_c$ | 0.390 | 0.1952 | $cm^{-1}$ |
| $\alpha_p$ | 69734.0 | 3309.0 | $keV^3/cm$ |

Figure 7:
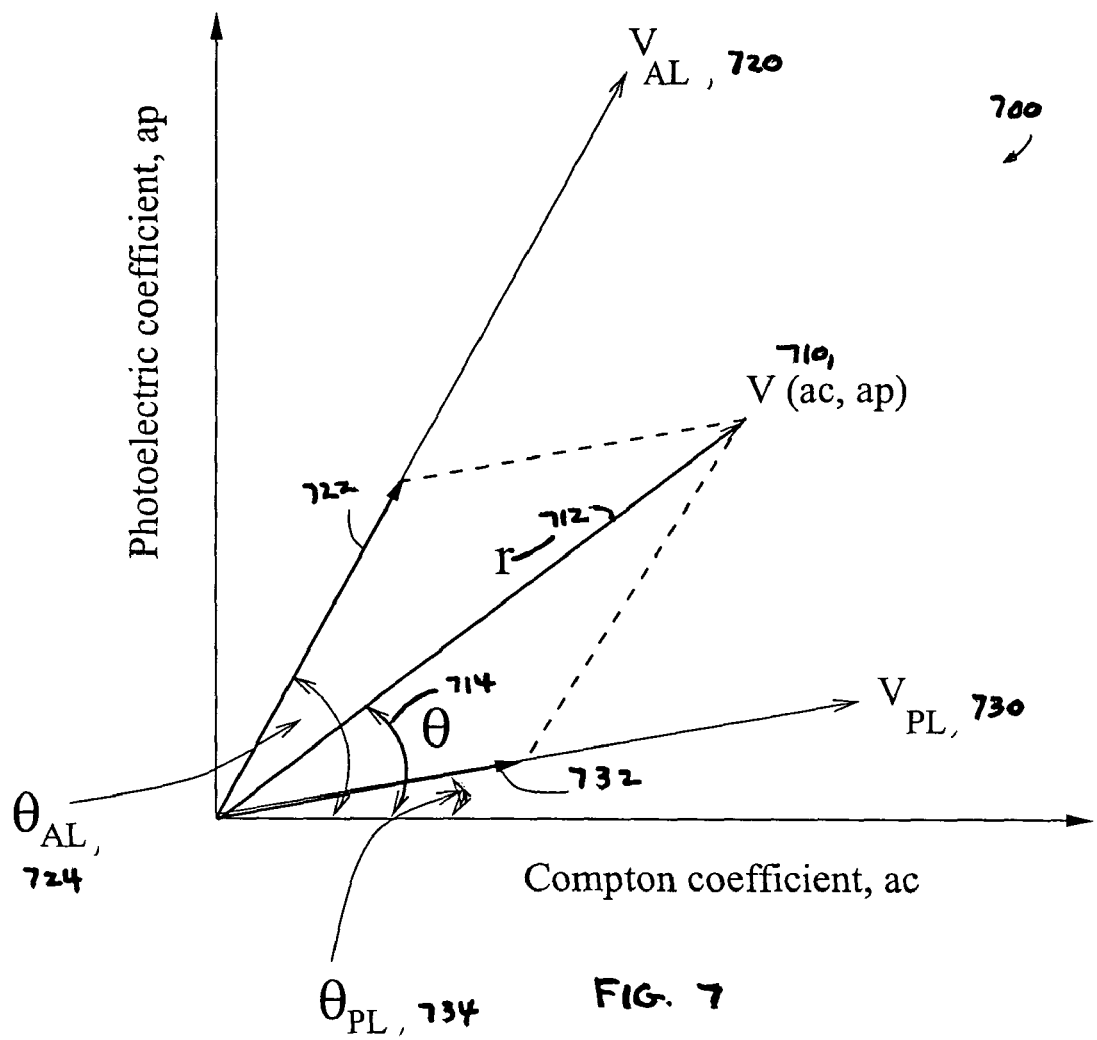
FIG. 7 is a vector representation of photoelectric and Compton coefficients for aluminum and plastic, in accordance with the illustrative embodiment.

The aluminum and plastic images are generated based on the following theory, demonstrated by the vector representation 700 shown in FIG. 7. A given pixel location (e.g., x, y) in $I_c$ and $I_p$ determines the coefficients $a_c(x, y)$, $a_p(x, y)$, which can be represented in polar coordinates (r 712, θ 714), as the vector V 710 in the two-dimensional space of Compton coefficients, $a_c$, and photoelectric coefficients, $a_p$, where:

$$r(V) = \sqrt{a_c(x, y)^2 + a_p(x, y)^2} \quad (28)$$

$$\theta(V) = \tan^{-1}\left(\frac{a_p(x, y)}{a_c(x, y)}\right)$$

In Equation 28, aluminum is represented by the vector $V_{Al}$ 720 represented in polar coordinates as ($r_{Al}$ 722, $\theta_{Pl}$ 724) and plastic is represented by the vector $V_{Pl}$ 730 represented in polar coordinates as ($r_{Pl}$ 734, $\theta_{Pl}$ 734) in FIG. 7. $V_{Al}$ and $V_{Pl}$ are defined to be the unit vectors along the directions of $V_{Al}$ and $V_{Pl}$. The image pair ($I_c$, $I_p$) can be processed into a pair of aluminum and plastic images, ($I_c$, $I_p$) wherein vectors determined by pixels in ($I_c$, $I_p$) are represented as admixtures of aluminum and plastic given by:

$$V = I_{Al}\hat{V}_{Al} + I_{Pl}\hat{V}_{Pl} \tag{29}$$

where $$I_{Pl} = r\cos\left[\frac{\pi}{2}\left(\frac{\theta - \theta_{Pl}}{\theta_{Al} - \theta_{Pl}}\right)\right] \tag{30}$$

$$I_{Al} = r\sin\left[\frac{\pi}{2}\left(\frac{\theta - \theta_{Pl}}{\theta_{Al} - \theta_{Pl}}\right)\right]$$

and $\theta_{Al}$ and $\theta_{Pl}$ are determined from the Compton and photoelectric coefficients of aluminum and plastic using Equation 28.

II. Details of the Decomposition

This section provides specific mathematical details of a dual energy decomposition algorithm with multi-step fitting, in accordance with the present invention. The inputs, parameters and outputs of the algorithm are listed, and then the mathematical details of the algorithm are presented below.

The inputs of the decomposition algorithm with multi-step fitting include low energy projection $P_L$ and high energy projection $P_H$, and the outputs include aluminum image $I_{Al}$ and plastic image $I_{Pl}$, in the illustrative embodiment. The various parameters are as follows:

| Symbol | Definition |
| --- | --- |
| $h_{Lij}$ | Fit coefficients used to determine low energy iso-transmission contours |
| $h_{Hij}$ | Fit coefficients used to determine high energy iso-transmission contours |
| $m_{Lj}$ | Fit coefficients used to determine the minimum value of $P_H$ for a given $P_L$ |
| $n_{Lj}$ | Fit coefficients used to determine the maximum value of $P_H$ for a given $P_L$ |
| $a_c^{Pl}$ | Compton coefficient of Plastic |
| $a_p^{Pl}$ | Photoelectric coefficient of Plastic |
| $a_c^{Al}$ | Compton coefficient of Aluminum |
| $a_p^{Al}$ | Photoelectric coefficient of Aluminum |
| $s_c$ | scale for decomposed Compton line integrals |
| $s_p$ | scale for decomposed photoelectric line integrals |
| $k_{ap}$ | Calibration scale factor for $A_p$ |

The preferred decomposition algorithm includes the following steps:

Step 1: Where $P_L$ is the input low energy projection data, compute the clamped value $P_{Lc}$ as:

$$P_{Lc} = \begin{cases} 0 & P_L < 0 \\ P_L & 0 \leq P_L \leq P_L^{\max} \\ P_L^{\max} & P_L > P_L^{\max} \end{cases} \tag{31}$$

Step 2: Given the value of PLC, calculate the values $P_H^{\min}$ and $P_H^{\max}$ as:

$$P_H^{\min}|_{P_{Lc}} = \sum_{j=0}^{j=6} m_{Lj} P_{Lc}^j \tag{32}$$

$$P_H^{\max}|_{P_{Lc}} = \sum_{j=0}^{j=6} n_{Lj} P_{Lc}^j$$

Step 3: Where $P_H$ is the input high energy projection data, compute the clamped value $P_{Hc}$ as:

$$P_{Hc} = \begin{cases} P_H^{\min}(P_{Lc}) & P_H < P_H^{\min}(P_{Lc}) \\ P_H & P_H^{\min}(P_{Lc}) \leq P_H \leq P_H^{\max} \\ P_H^{\max} & P_H > P_H^{\max}(P_{Lc}) \end{cases} \tag{33}$$

Step 4: Given the input coefficients $h_{Lij}$, generate the coefficients $g_{Li}$ of the low energy iso-transmission contour as:

$$g_{Li} = \sum_{j=0}^{j=6} h_{Lij} P_{Lc}^j \quad i = 0, 1, 2 \tag{34}$$

Step 5: Given the input coefficients $h_{Hij}$, generate the coefficients $g_{Hi}$ of the high energy iso-transmission contour as:

$$g_{Hi} = \sum_{j=0}^{j=6} h_{Hij} P_{Lc}^j \quad i = 0, 1, 2 \tag{35}$$

Step 6: Determine the intersection of the iso-transmission contours corresponding to $P_{Lc}$ and $P_{Hc}$ as the solution to the equations:

$$g_{L0} + g_{L1}A_c + g_{L2}A_c^2 = g_{H0} + g_{H1}A_c + g_{H2}A_c^2 \tag{36}$$

as follows:

1) Calculate the discriminant D as:

$$D = (g_{L1} - g_{H1})^2 - 4(g_{L0} - g_{H0})(g_{L2} - g_{H2}) \tag{37}$$

2) Clamp the value of D to $D_c$ calculated as:

$$D_c = \begin{cases} D & D \geq 0 \\ 0 & D < 0 \end{cases} \tag{38}$$

This step is performed because, in some cases, negative values of D could be calculated due to noise and numerical errors in the data.

3) Determine the value of $A_c$ at the intersection of the high and low energy contours as the smaller of the roots determined by the equation:

$$A_c = \frac{-(g_{L1} - g_{H1}) \pm \sqrt{D_c}}{2(g_{L2} - g_{H2})} \quad (39)$$

Note that the negative solution from the above equation is clamped to 0 because $A_c$ is a line integral, which must be non-negative.

4) Calculate the value of $A_p$ using the equation:

$$A_p = g_{L0} + g_{L1} A_c + g_{L2} A_c^2 \quad (40)$$

5) Calculate $A_{pc}$ as the clamped value of $A_p$:

$$A_{pc} = \begin{cases} A_p & A_p \geq 0 \\ 0 & A_p < 0 \end{cases} \quad (41)$$

Step 7: Given the scale factors $s_c$ and $s_p$, calculate the scaled projections as $A_{cs}$ and $A_{ps}$:

$$A_{cs} = s_c A_c$$

Step 8: Reconstruct Compton and photoelectric images $I_c$ and $I_p$, from the values $A_{cs}$ and $A_{ps}$ using filtered backprojection.

Step 9: This is an optional step. Solve the images $I_c$ and $I_p$ on a pixel-by-pixel basis to determine $I_{Al}$ and $I_{Pl}$, as previously described. The equations are repeated here for convenience. Let (x, y) be the location of a pixel. The intensity of the pixel in the images ($I_{Al}$, $I_{Pl}$) are calculated as:

$$I_{Pl}(x, y) = r(x, y) \cos\left[\frac{\pi}{2}\left(\frac{\theta(x, y) - \theta_{Pl}}{\theta_{Al} - \theta_{Pl}}\right)\right] \quad (43)$$

$$I_{Al}(x, y) = r(x, y) \sin\left[\frac{\pi}{2}\left(\frac{\theta(x, y) - \theta_{Pl}}{\theta_{Al} - \theta_{Pl}}\right)\right]$$

where $$r(x, y) = \sqrt{I_c(x, y)^2 + I_p(x, y)^2} \quad (44)$$

$$\theta(x, y) = \tan^{-1}\left(\frac{I_p(x, y)}{I_c(x, y)}\right)$$

and $$\theta_{Pl} = \tan^{-1}\left(\frac{s_p a_p^{Pl}/k_{ap}}{s_c a_c^{Pl}}\right) \quad (45)$$

$$\theta_{Al} = \tan^{-1}\left(\frac{s_p a_p^{Al}/k_{ap}}{s_c a_c^{Al}}\right)$$

III. Overview of Calibration

This section provides the details of a calibration procedure, which generates parameters use by the dual energy decomposition algorithm with multi-step fitting. The calibration procedure includes the following steps.

Step 1: Simulated projection data are generated for known values of high and low energy projections.

Step 2: An iso-transmission contour is determined for each projection.

Step 3: For each iso-transmission contour, the photoelectric line integral is fit using a quadratic function of the Compton line integral.

Step 4: Fit coefficients from the quadratic function are determined for several projection values.

Step 5: The variation of each fit coefficient with projection value is described by a polynomial function.

Step 6: The fit coefficients of the polynomial function are stored for high and low energy values and input to the decomposition algorithm, in accordance with the present invention.

The inputs of the calibration procedure are the simulated low energy input spectrum $S_L$ and the simulated high energy input spectrum $S_H$. The outputs include the fit coefficients $h_{Lij}$ used to determine the low energy iso-transmission contours, the fit coefficients $h_{Hij}$ used to determine the high energy iso-transmission contours, the fit coefficients $m_{Lj}$ used to determine the minimum value of $P_H$ for a given $P_L$, and the fit coefficients $n_{Lj}$ used to determine the maximum value of $P_H$ for a given $P_L$.

The parameters of the calibration procedure are as follows:

| Symbol | Definition |
| --- | --- |
| $a_c^{Pl}$ | Compton coefficient of plastic |
| $a_p^{Pl}$ | Photoelectric coefficient of plastic |
| $N_{iso}$ | Number of points generated per iso-transmission line |
| $t_{Pl}^{min}$ | Minimum thickness of plastic used in calibration |
| $t_{Pl}^{max}$ | Maximum thickness of plastic used in calibration |
| $d_{Pl}$ | Thickness increment |
| $k_{ap}$ | Calibration scale factor for $A_p$ |

Below is described the mathematics for generating iso-transmission contours for low-energy projections. The same procedure is used to generate iso-transmission contours for high-energy projections.

Step 1: Given the parameters $t_{Pl}^{min}$, $t_{Pl}^{max}$ and $d_{Pl}$, compute the number of projection values $n_{proj}$ as follows:

$$n_{proj} = \frac{t_{Pl}^{max} - t_{Pl}^{min}}{d_{Pl}} \quad (46)$$

Step 2: For each value of $t_{Pl}[n]$:

$$t_{Pl}[n] = t_{Pl}^{min} + nd_{Pl}, \quad n = 0, \ldots, n_{proj} \quad (47)$$

compute the low-energy projection $P_L[n]$ as follows, using Equation 14:

$$P_L[n] = f_L(a_c^{Pl} t_{Pl}[n], a_p^{Pl} t_{Pl}[n]) \quad (48)$$

Step 3: For each value of the low-energy projection $P_L[n]$, compute the iso-transmission contour. The iso-transmission contour is a set of ordered pairs of ($A_c[l][n]$, $A_p[l][n]$), where $l=0, \ldots, N_{iso}$, all of which produce the value $P_L[n]$. There are generally three steps involved in computing each iso-transmission contour:

1) Compute $A_c[0][n]$, which is the maximum value of $A_c$ for low-energy projection $P_L[n]$, by iteratively solving the following equation:

$$f_L(A_c[0][n], 0) = P_L[n] \quad (49)$$

2) Compute $A_c[l][n]$ for each l as follows:

$$A_L[l][n] = A_c[0][n] - l\left(\frac{A_c[0][n]}{N_{iso}}\right), \quad l = 1, \ldots, N_{iso} \quad (50)$$

3) Compute the associated $A_p[l][n]$ by iteratively solving the following equation:

$$f_L(A_c[l][n], A_p[l][n]) = P_L[n], \, l=1, \ldots, N_{iso} \quad (51)$$

Note that $A_p[0][n]=0$. Below is a more detailed description of the preferred iterative method used to solve Equations 49 and 51.

4) Each $A_p[l][n]$ is scaled as follows:

$$A_{pk}[l][n] = A_p[l][n]/k_{ap} \quad (52)$$

where $k_{ap}$ is the scale factor provided to the calibration procedure. The scale factor $k_{ap}$ is used to obtain similar ranges of values among $A_p$ and $A_c$.

Step 4: For each iso-transmission contour (given n), there are $N_l$ ordered pairs of $(A_c[l][n], A_p[l][n])$. The $N_l$ ordered pairs are fit using the quadratic function:

$$A_{pk} = g_{L0}[n] + g_{L1}[n]A_c + g_{L2}[n]A_c^2 \quad (53)$$

Step 5: Fit the coefficients of the quadratic function using sixth-order polynomial functions of the low-energy projection value $P_L$:

$$g_{Li} \sum_{j=0}^{6} h_{Lij} P_L^j, \quad i = 0, 1, 2 \quad (54)$$

The fitting is performed using a chi-squared minimization routine. This routine is known in the mathematical arts, and is described in W. H. Press, S. A. Teukolsky, W. T. Vetterling and B. P. Flannery, *Numerical Recipes in C, The Art of Scientific Computing,* 2nd Ed. (Cambridge University Press, New York, N.Y., 1992), Chap 15, pp. 681–706.

Step 6: In addition to the iso-transmission contour, compute the minimum and maximum values of the corresponding high-energy projection $P_H^{min}[n]$ and $P_H^{max}[n]$ for each $P_L[n]$, as follows:

$$P_H^{min}[n] = f_H(A_c[0], 0)$$

$$P_H^{max}[n] = f_H(0, A_p[N_{iso}]) \quad (55)$$

Step 7: Fit the minimum and the maximum $P_H$ to sixth-order polynomial functions of $P_L$ as follows:

$$P_H^{min} = \sum_{j=0}^{6} m_{Lj} P_L^j$$

$$P_H^{max} = \sum_{j=0}^{6} n_{Lj} P_L^j \quad (56)$$

The steps (1) through (6) above is repeated for obtaining coefficients $h_{Hij}$ for generating the iso-transmission contours of the high-energy projections $P_H$.

Step 8: The fit coefficients $h_{Lij}$, $h_{Hij}$, $m_{Lj}$, and $n_{Lj}$ are stored for use by the decomposition algorithm.

The solution of Equations 49 and 51 is determined using the following iterative algorithm. The algorithm is described for a single low energy iso-transmission curve or contour for projection $P_o$, for a single value of the Compton line integral $A_c$. The same procedure is applied to determine values for the high-energy iso-transmission curve or contour.

Step 1: For the value of the Compton line integral $A_c$, two initial estimations for the photoelectric line integral are made to obtain projections with magnitudes greater than and less than $P_o$. Let the estimations be designated $A_{p1}$ and $A_{p2}$, respectively, wherein:

$$A_{p1} = A_c$$

$$A_{p2} = -5 \quad (57)$$

Note that the negative value of $A_{p2}$ is chosen to obtain a projection value that is greater than $P_o$. The positive value of $A_{p1} = A_c$ is chosen to obtain a projection value that is lesser than $P_o$.

Step 2: The following steps are iterated.

1) For iteration i, the values of the corresponding low-energy projections are calculated using Equation 14.

$$P_1^i = F_L(A_c, A_{p1}^i)$$

$$P_2^i = F_L(A_c, A_{p2}^i)$$

$$P_m^i = F_L(A_c, A_{pm}^i) \quad (58)$$

where the superscript i is used to represent values from the i iteration and:

$$A_{pm}^i = \frac{A_{p1}^i + A_{p2}^i}{2} \quad (59)$$

2) For iteration i, calculate new values for $A_{p1}^i$ and $A_{p2}^i$ as follows:

$$A_{p1}^i = \begin{cases} A_{pm}^{i-1} & \text{if } P_m^{i-1} < P_o \\ A_{p1}^{i-1} & \text{otherwise} \end{cases} \quad (60)$$

$$A_{p2}^i = \begin{cases} A_{pm}^{i-1} & \text{if } P_m^{i-1} > P_o \\ A_{p2}^{i-1} & \text{otherwise} \end{cases} \quad (61)$$

Step 3: Repeat the Steps 2(1) and 2(2) until the following condition is satisfied:

$$P_2^i - P_1^i < \epsilon \quad (62)$$

where $\epsilon=0.1$ is the tolerance for convergence.

The value of $A_{pm}^i$ is then returned.

While the foregoing has described what are considered to be the best mode and/or other preferred embodiments, it is understood that various modifications may be made therein and that the invention or inventions may be implemented in various forms and embodiments, and that they may be applied in numerous applications, only some of which have been described herein. For example, reference was made variously to use of polynomial equations, quadratic equations and equations having variables raised to other powers. However, in other embodiments, appropriate equations could take other forms, such as any of a number of forms of parametric equations. That is, as will be appreciated by those skilled in the mathematical arts, there can be various manners of representing or modeling physical, electrical, mechanical and other sciences and the equations used to do so can be made more or less complex given whatever assumptions are made with respect to the parameters related to such equations.

As used herein, the terms "includes" and "including" mean without limitation. It is intended by the following claims to claim any and all modifications and variations that fall within the true scope of the inventive concepts.

What is claimed is:

1. A method for decomposition of projection data acquired by scanning a set of objects using at least two x-ray spectra, the projection data including low energy projections ($P_L$) and high energy projections ($P_H$), said method comprising:
   A. solving the projections $P_L$ and $P_H$ to determine a photoelectric line integral ($A_p$) component of attenuation and a Compton line integral ($A_c$) component of attenuation of the set of scanned objects using multi-step fitting; and
   B. reconstructing a Compton image $I_c$ and a photoelectric image $I_p$ from $A_c$ and $A_p$.

2. The method of claim 1, further including, prior to step A, performing a calibration procedure using simulated data or measured data or some combination of simulated and measured data.

3. The method of claim 1, further including, prior to step A, performing a calibration procedure, wherein said calibration procedure includes generating low energy iso-transmission contours for known values of $P_L$ at known values of $A_p$ and at known values of $A_c$.

4. The method of claim 3, wherein said calibration procedure includes, for each of said low energy iso-transmission contours, fitting $A_p$ to a polynomial function $g_L(A_c)$, wherein $g_L$ is a polynomial function that represents the shape of the contour.

5. The method of claim 4, wherein $g_L$ includes a set of coefficients $g_{Li}$ determined at said known values of $P_L$ and said calibration procedure includes fitting the values of each coefficient $g_{Li}$ to a polynomial function $h_{Li}(P_L)$.

6. The method of claim 1, wherein said calibration procedure includes computing minimum and maximum values of $P_H$ for each of said low-energy iso-transmission contours as a function of $P_L$.

7. The method of claim 6, wherein said calibration procedure includes fitting the minimum values of $P_H$ to a polynomial function $m_L(P_L)$.

8. The method of claim 6, wherein said calibration procedure includes fitting the maximum values of $P_H$ to a polynomial function $n_L(P_L)$.

9. The method of claim 1, wherein said calibration procedure includes generating high energy iso-transmission contours for known values of $P_H$ at known values of the $A_p$ and at known values of the $A_c$.

10. The method of claim 9, wherein said calibration procedure includes, for each of said high energy iso-transmission contours, fitting $A_p$ to a polynomial function $g_H(A_c)$, wherein $g_H$ is a polynomial function that represents the shape of the contour for a given $P_H$.

11. The method of claim 10, wherein said $g_H$ includes a set of coefficient $g_{Hi}$ determined at said known values of $P_H$ and said calibration procedure includes fitting the values of each coefficient $g_{Hi}$ to a polynomial function $h_{Hi}(P_H)$.

12. The method of claim 1, wherein step A includes generating a low energy iso-transmission contour corresponding to $P_L$ and a high energy iso-transmission contour corresponding to $P_H$.

13. The method of claim 12, wherein step A includes determining the values of the $A_p$ and $A_c$ at the intersection of said low energy iso-transmission contour and the high energy iso-transmission contour.

14. The method of claim 13, wherein the intersection of the low energy iso-transmission contour and the high energy iso-transmission contour is determined by equating a first polynomial function $g_L(A_c)$ representing said low energy iso-transmission contour, wherein $g_L$ is a polynomial function that represents the shape of the contour of $P_L$, with a second polynomial function $g_H(A_c)$ representing said high energy iso-transmission contour, wherein $g_H$ is a polynomial function that represents the shape of the contour for a given $P_H$.

15. The method of claim 12, further including computing a modified value of the input low energy projection data ($P_{Lc}$) and a modified value of the input high energy projection data ($P_{Hc}$), wherein each of said modified values $P_{Lc}$ and $P_{Hc}$ are clamped to be bounded between two values.

16. The method of claim 15, including representing the low energy iso-transmission contour with a polynomial function $g_L$ and determining a set of coefficients of $g_L$ as a function of $P_{Lc}$.

17. The method of claim 15, including representing the high energy iso-transmission contour with a polynomial function $g_H$ and determining a set of coefficients of $g_H$ as a function of $P_{Hc}$.

18. The method of claim 15, further including, prior to step A, generating calibration data using $P_L$, wherein $P_{Lc}$ is computed by clamping the value of $P_L$ to lie between 0 and the maximum value of $P_L$ used to generate said calibration data.

19. The method of claim 15, wherein the modified value $P_{Hc}$ is determined by clamping the value of $P_H$ to lie between a minimum value of $P_H(P_{Hmin})$ and a maximum value of $P_H(P_{Hmax})$.

20. The method of claim 19, including determining $P_{Hmin}$ as a function of $P_{Lc}$ and a polynomial function $n_L$ and determining $P_{Hmax}$ as a function of $P_{Lc}$ and a polynomial function $m_L$, wherein $m_L$ is a polynomial function that determines $P_{Hmin}$ for a given value of $P_{Lc}$ and wherein $n_L$ is a polynomial function that determines $P_{Hmin}$ for a given value of $P_{Lc}$.

21. The method of claim 1, wherein step A includes calculating a scaled Compton line integral value ($A_{cs}$) as a function of a scale factor $s_c$ and $A_c$ and calculating a scaled photoelectric line integral value ($A_{ps}$) as a function of a scale factor $s_p$ and $A_{ps}$.

22. The method of claim 21, wherein step B includes constructing said $I_c$ and said $I_p$ as a function of said $A_{cs}$ and said $A_{ps}$.

23. The method of claim 1, further including, after step B, determining an image of a basis function $X(I_X)$ and a basis function $Y(I_Y)$, by solving $I_c$ and $I_p$ on a pixel-by-pixel basis, wherein the basis functions $X(I_X)$ and $Y(I_Y)$ are functions linearly combined to determine the pixel intensities in $I_c$ and $I_p$.

24. A method for decomposition of projection data acquired by scanning a set of objects using at least two x-ray spectra, said projection data including low energy projection data ($P_L$) and high energy projection data ($P_H$), said method comprising:
   A. performing a calibration procedure using at least some simulated data or measured data or a combination of simulated and measured data, including:
      i. generating low energy iso-transmission contours for known values of $P_L$ and high energy iso-transmission contours for known values of $P_H$;

ii. generating a polynomial $g_L$ that represents the shape of the low energy iso-transmission contour for each $P_L$, wherein $g_L$ includes a set of coefficients $g_{Li}$ determined at said known values of $P_L$;

iii. generating a polynomial $g_H$ that represents the shape of the high energy iso-transmission contour for each $P_H$, wherein $g_H$ includes a set of coefficients $g_{Hi}$ determined at said known values of $P_H$;

iv. generating polynomials $h_L$ that represents the variation of the coefficients of the polynomial $g_L$ as a function of $P_L$;

v. generating polynomials $h_H$ that represents the variation of the coefficients of the polynomial $g_H$ as a function of $P_H$;

vi. determining the minimum and maximum values of $P_H$ for each transmission line corresponding each $P_L$;

vii. generating a polynomial $m_H$ that represents the variation of the minimum value of $P_H$ as a function of $P_L$; and viii. generating a polynomial $n_H$ that represents the variation of the maximum value of $P_H$ as a function of $P_L$;

B. solving the projections $P_L$ and $P_H$ to determine a photoelectric line integral ($A_p$) component of attenuation and a Compton line integral ($A_c$) component of attenuation of the set of scanned objects using a multi-step fitting procedure, including:

i. computing the values of each coefficient $g_{Li}$ using a polynomial function $h_{Li}(P_L)$ and computing the values of each coefficient $g_{Hi}$ using a polynomial function $h_{Hi}(P_H)$; and ii. determining $A_c$ and $A_p$ as a function of $P_L$ and $P_H$, using the coefficients of $g_L$ and the coefficients of $g_H$; and C. reconstructing a Compton image $I_c$ and a photoelectric image $I_p$ from $A_c$ and $A_p$.

25. The method of claim 24, further including, after step C, determining an image of a basis function $X(I_X)$ and a basis function $Y(I_Y)$, by solving image $I_c$ and image $I_p$ on a pixel-by-pixel basis.

26. A system for decomposing projection data for a set of scanned objects acquired using at least two x-ray spectra, said system comprising:

A. media for storing low energy projection data ($P_L$) and high energy projection data ($P_H$);

B. a decomposition module configured to determine a photoelectric line integral ($A_p$) component of attenuation and a Compton line integral ($A_c$) component of attenuation for $P_L$ and $P_H$ using multi-step fitting; and C. an image construction module configured to construct a Compton image ($I_c$) and a photoelectric image ($I_p$) from the $A_p$ and $A_c$.

27. The system of claim 26, wherein the decomposition module includes:

D. a calibration module configured to calibrate the decomposition module using at least some simulated data or measured data or a combination of simulated data and measured data.

28. The system of claim 27, wherein the calibration module is configured to generate low energy iso-transmission contours for known values of $P_L$ at known values of $A_p$ and at known values of $A_c$.

29. The system of claim 28, wherein the calibration module is configured, for each of said low energy iso-transmission contours, to fit $A_p$ to a polynomial function $g_L(A_c)$, wherein $g_L$ is a polynomial function that represents the shape of the contour.

30. The system of claim 29, wherein $g_L$ includes a set of coefficients $g_{Li}$ determined at said known values of $P_L$ and the calibration module is configured to fit said set of coefficients $g_{Li}$ to a polynomial function $h_{Li}(P_L)$.

31. The system of claim 28, wherein the calibration module is configured to compute the minimum and maximum values of $P_H$ for each of the low-energy iso-transmission contours corresponding to $P_L$.

32. The system of claim 28, wherein the calibration module is configured to fit the minimum values of $P_H$ to a polynomial function $m_L(P_L)$.

33. The system of claim 28, wherein the calibration module is configured to fit the maximum values of $P_H$ to a polynomial function $n_L(P_L)$.

34. The system of claim 27, wherein the calibration module is configured to generate high energy iso-transmission contours for known values of $P_H$ at known values of $A_p$ and at known values of $A_c$.

35. The system of claim 34, wherein the calibration module is configured, for each of said high energy iso-transmission contours, to fit $A_p$ to a polynomial function of $g_H(A_c)$, wherein $g_H$ is a polynomial function that represents the shape of the contour for a given $P_H$.

36. The system of claim 34, wherein $g_H$ includes a set of coefficients $g_{Hi}$ determined at said known values of $P_H$ and the calibration module is configured to fit said set of coefficients $g_{Hi}$ to a polynomial function $h_{Hi}(P_H)$.

37. The system of claim 26, wherein the decomposition module is configured to generate a low energy iso-transmission contour corresponding to $P_L$ and a high energy iso-transmission contour corresponding to $P_H$.

38. The system of claim 37, wherein the decomposition module is configured to determine the values of $A_p$ and $A_c$ at the intersection of said low energy iso-transmission contour and the high energy iso-transmission contour.

39. The method of claim 37, wherein the decomposition module is configured to compute a modified value of the input low energy projection data ($P_{Lc}$) and a modified value of the input high energy projection data ($P_{Hc}$), and configured to clamp said modified values $P_{Lc}$ and $P_{Hc}$ between two values.

40. The system of claim 39, wherein the decomposition module is configured to clamp the values of $P_L$ to lie between 0 and the maximum value of $P_L$ used to generate a set of calibration data and to compute the modified value $P_{Lc}$ as a function of the clamped values of $P_L$.

41. The system of claim 39, wherein the decomposition module is configured to clamp $P_{Hc}$ between a minimum value of $P_H(P_{Hmin})$ and a maximum value of $P_H(P_{Hmax})$.

42. The system of claim 41, wherein the decomposition module is configured to determine $P_{Hmin}$ as a function of $P_{Lc}$ and a polynomial $n_L$ and to determine $P_{Hmax}$ as a function of $P_{Lc}$ and a polynomial $m_L$, wherein $m_L$ is a polynomial function representing the coefficients of $P_L$ for the minimum values of $P_H$ and wherein $n_L$ is a polynomial function representing the coefficients of $P_L$ for the maximum values of $P_H$.

43. The system of claim 26, wherein the decomposition module is configured to calculate a scaled Compton line integral value ($A_{cs}$) as a function of a scale factor $s_c$ and $A_c$ and to calculate a scaled photoelectric line integral value ($A_{ps}$) as a function of a scale factor sp and $A_{ps}$.

44. The system of claim 26, wherein the image reconstruction module is configured to reconstruct said $I_c$ and said $I_p$ as a function of said $A_{cs}$ and said $A_{ps}$.

45. The system of claim 26, wherein the image reconstruction module is configured to determine an image of a basis function $X(I_X)$ and of a basis function $Y(I_Y)$, by solving $I_c$ and $I_p$ on a pixel-by-pixel basis, wherein the basis functions $X(I_X)$ and $Y(I_Y)$ are functions linearly combined to determine the pixel intensities in $I_c$ and $I_p$.

46. A system for decomposing projection data for a set of scanned objects acquired using at least two x-ray spectra, said system comprising:

A. media for storing low energy projection data ($P_L$) and high energy projection data ($P_H$);

B. a calibration module configured to calibrate the decomposition module using at least some simulated data or measured data or a combination of simulated and measured data, and configured to:
   i. generate a low energy iso-transmission contour corresponding to $P_L$ and a high energy iso-transmission contour corresponding to $P_H$;
   ii. generate a polynomial $g_L$ that represents the shape of the low energy iso-transmission contour, wherein $g_L$ includes a set of coefficients $g_{Li}$ determined at said known values of $P_L$;
   iii. generate a polynomial $g_H$ that represents the shape of the high energy iso-transmission contour, wherein $g_H$ includes a set of coefficients $g_{Hi}$ determined at said known values of $P_H$;
   iv. generate polynomials $h_L$ that represents the variation of the coefficients of the polynomial $g_L$ as a function of $P_L$;
   v. generate polynomials $h_H$ that represents the variation of the coefficients of the polynomial $g_H$ as a function of $P_H$;
   vi. determine the minimum and maximum values of $P_H$ for each transmission line corresponding each $P_L$;
   vii. generate a polynomial $m_H$ that represents the variation of the minimum value of $P_H$ as a function of $P_L$; and
   viii. generate a polynomial $n_H$ that represents the variation of the maximum value of $P_H$ as a function of $P_L$;

C. a decomposition module configured to determine a photoelectric line integral ($A_p$) component of attenuation and a Compton line integral ($A_c$) component of attenuation for $P_L$ and $P_H$ using multi-step fitting, and configured to:
   i. compute the values of each coefficient $g_{Li}$ using a polynomial function $h_{Li}(P_L)$ and to compute the values of each coefficient $g_{Hi}$ using a polynomial function $h_{Hi}(P_H)$; and
   ii. determine $A_c$ and $A_p$ as a function of $P_L$ and $P_H$ using the coefficients of $g_L$ and the coefficients of $g_H$; and D. an image reconstruction module configured to reconstruct a Compton image ($I_c$) and a photoelectric image ($I_p$) from the $A_p$ and $A_c$.

47. The system of claim 46, wherein the image construction module is configured to determine an image of a basis function $X(I_X)$ and of a basis function $Y(I_Y)$, by solving image $I_c$ and image $I_p$ on a pixel-by-pixel basis.

* * * * *